(12) United States Patent
Lim (10) Patent No.: US 10,620,046 B2
(45) Date of Patent: Apr. 14, 2020

(54) LENS ASSEMBLY WITH INTEGRATED LIGHT SOURCE AND SPECTROSCOPIC ANALIZER INCLUDING THE SAME

(71) Applicant: SUNFOREST Co., Ltd., Incheon (KR)

(72) Inventor: Dong Cheol Lim, Incheon (KR)

(73) Assignee: SUNFOREST CO., LTD., Incheon (KR)

(*) Notice: Subject to any disclaimer, the term of this patent is extended or adjusted under 35 U.S.C. 154(b) by 0 days.

(21) Appl. No.: 16/021,445

(22) Filed: Jun. 28, 2018

(65) Prior Publication Data
US 2018/0321082 A1 Nov. 8, 2018

Related U.S. Application Data (63) Continuation of application No. PCT/KR2016/014181, filed on Dec. 5, 2016.

(30) Foreign Application Priority Data

Dec. 28, 2015 (KR) .......................... 10-2015-0187436

(51) Int. Cl.

| | | |
|---|---|---|
| G01J 3/02 | (2006.01) | |
| G01J 3/28 | (2006.01) | |
| G01N 21/359 | (2014.01) | |
| G01J 3/10 | (2006.01) | |
| G01J 3/18 | (2006.01) | |
| G01N 33/02 | (2006.01) | |

(52) U.S. Cl.
CPC .......... *G01J 3/0208* (2013.01); *G01J 3/0243* (2013.01); *G01J 3/0262* (2013.01); *G01J 3/0291* (2013.01); *G01J 3/108* (2013.01); *G01J 3/18* (2013.01); *G01J 3/28* (2013.01); *G01N 21/359* (2013.01); *G01N 33/025* (2013.01); *G01N 2201/0221* (2013.01)

(58) Field of Classification Search
CPC ........ G01J 3/0208; G01J 3/0262; G01J 3/108; G01J 3/02; G01J 3/28; G01J 3/359
See application file for complete search history.

(56) References Cited

U.S. PATENT DOCUMENTS

| | | | | |
|---|---|---|---|---|
| 4,131,540 A | * | 12/1978 | Husome .................. | B07C 5/342 209/582 |
| 4,350,442 A | * | 9/1982 | Arild ...................... | B07C 5/3425 209/577 |
| 4,897,536 A | * | 1/1990 | Miyoshi ................. | G01B 11/00 250/201.6 |
| 6,137,581 A | * | 10/2000 | Kimura ................. | G01N 21/274 209/581 |

(Continued)

FOREIGN PATENT DOCUMENTS

| KR | 10-2004-0015157 A | 2/2004 |
|---|---|---|
| KR | 10-1397158 B1 | 5/2014 |

*Primary Examiner* — Sang H Nguyen
(74) *Attorney, Agent, or Firm* — Rabin & Berdo, P.C.

(57) ABSTRACT

A lens assembly with an integrated light source includes a light source configured to emit light to an object to be measured, a lens configured to receive light diffused and reflected from inside the object, a through hole formed at a center of the lens, in which the light source is arranged, and an internal light shielding unit arranged between the light source and an inner wall of the through hole, wherein a front portion of the internal light shielding unit protrudes from a surface of the lens toward the object.

12 Claims, 8 Drawing Sheets

(56) References Cited

U.S. PATENT DOCUMENTS

| | | | | |
|---|---|---|---|---|
| 7,068,368 | B1* | 6/2006 | Nagayoshi | G01N 21/27 209/577 |
| 2002/0011567 | A1* | 1/2002 | Ozanich | G01J 3/02 250/326 |
| 2003/0213894 | A1* | 11/2003 | Muller | B23Q 17/225 250/221 |
| 2004/0130720 | A1* | 7/2004 | Maeda | G01J 3/02 356/419 |
| 2006/0118726 | A1* | 6/2006 | Kawabata | G01N 21/359 250/358.1 |
| 2007/0229832 | A1* | 10/2007 | Maeda | B07C 5/3416 356/419 |
| 2009/0147260 | A1* | 6/2009 | Costa | G01N 21/314 356/433 |
| 2015/0332908 | A1* | 11/2015 | Blondia | H01J 61/16 313/111 |

* cited by examiner

LENS ASSEMBLY WITH INTEGRATED LIGHT SOURCE AND SPECTROSCOPIC ANALIZER INCLUDING THE SAME

CROSS-REFERENCE TO RELATED APPLICATIONS

This application is a continuation of International Application No. PCT/KR2016/014181, filed Dec. 5, 2016, which is based upon and claims the benefit of priority from Korean Patent Application No. 10-2015-0187436, filed Dec. 28, 2015, which is now Korean Patent No. 10-1690073, the contents of which are incorporated herein by reference in their entirety.

BACKGROUND

1. Field

The present invention relates to a lens assembly with an integrated light source and a spectroscopic analyzing apparatus including the lens assembly.

2. Description of the Related Art

A near-infrared spectroscopic analyzing apparatus generally includes a broadband light source for emitting light to an object to be tested, a light collecting member for collecting (focusing) light reflected mainly from inside the object, and a spectrometer for detecting absorbance wavelength spectra of the light collected (focused) by the light collecting member.

This type of spectroscopic analyzing apparatus creates a correlation between the absorbance wavelength spectra and components of the object with a calibration model equation using regression analysis and appropriate mathematical pre-processing and correction, thus being capable of measuring physical and chemical properties inside the object in a nondestructive manner without a pretreatment of the object.

An example of such spectroscopic analyzing apparatus is an apparatus for measuring sugar contents of fruits in a nondestructive manner.

The internal quality of a fruit, such as the sugar contents, not only has a large individual difference due to varieties, harvest time, and differences in cultivation environments and techniques but also has a difference even among fruits harvested from the same tree. Therefore, it can be said that it is indispensable to develop an appropriate cultivation technique through a real-time sugar contents measurement of a fruit at a cultivation stage or stages before and after harvest and an apparatus for measuring the sugar contents in a nondestructive manner as a means for improving the fruit quality by determining proper time of harvesting.

A conventional technique related to a spectroscopic apparatus for measuring the sugar contents of a fruit in a nondestructive manner includes a portable apparatus for testing internal quality described in Korean Patent Laid-Open Publication No. 10-2004-0015157.

The portable apparatus for testing internal quality described in Korean Patent Laid-Open Publication No. 10-2004-0015157 focuses light, which is emitted from a light source to an object to be tested and diffused and reflected from inside the object, with a bunch of optical fibers and transmits the focused light to a spectrometer.

The portable apparatus for testing internal quality described in Korean Patent Laid-Open Publication No. 10-2004-0015157 employs a bundle of optical fibers parallelly arranged at an input slit of the spectrometer, causing problems of securing a relatively large space, arranging the optical fibers in the secured space, which is not easy, and coupling the diffused and reflected light into the optical fibers, which is not easy, either.

Another example of the spectroscopic apparatus for measuring the sugar contents of a fruit in a nondestructive manner is a portable apparatus for measuring sugar contents of tangerine in a nondestructive manner described in Korean Patent No. 10-1397158.

The portable apparatus for measuring sugar contents of tangerine in a nondestructive manner described in Korean Patent No. 10-1397158 includes a light emitting unit for emitting light to an object and a light receiving unit (lens) for focusing light diffused and reflected from inside the object, arranged laterally in parallel.

With a structure in which the light emitting unit and the light receiving unit are arranged laterally in parallel, when a distance between the light emitting unit and the light receiving unit increases, a measurement result is greatly affected by size and shape of the object, and when the distance between the light emitting unit and the light receiving unit decreases, a depth of penetration of the light into the object decreases, generating a light interference, which can cause a large error in measured sugar contents. In addition, as this structure arranges the light emitting unit and the light receiving unit in parallel, it is required to secure a space for mounting each of the light emitting unit and the light receiving unit, resulting in an increase of a volume of the spectroscopic analyzing apparatus.

SUMMARY

According to some embodiments of the present invention, a lens assembly with an integrated light source includes a light source configured to emit light to an object to be measured, a lens configured to receive light diffused and reflected from inside the object, a through hole formed at a center of the lens, in which the light source is arranged, and an internal light shielding unit arranged between the light source and an inner wall of the through hole, wherein a front portion of the internal light shielding unit protrudes from a surface of the lens toward the object.

Further, according to some embodiments of the present invention, a spectroscopic analyzing apparatus includes a body case, a head unit arranged at a first end of the body case, a spectrometer arranged in the body case, the spectrometer including an input slit having a predetermined numerical aperture. The head unit includes a lens assembly with an integrated light source. The lens assembly includes a light source configured to emit light to an object to be measured, a lens configured to receive light diffused and reflected from inside the object, a through hole formed at a center of the lens, in which the light source is arranged, and an internal light shielding unit arranged between the light source and an inner wall of the through hole, wherein a front portion of the internal light shielding unit protrudes from a surface of the lens toward the object.

DETAILED DESCRIPTION OF THE SOME EMBODIMENTS

Exemplary embodiments of the present invention are described in detail below with reference to the accompanying drawings.

Figure 1:
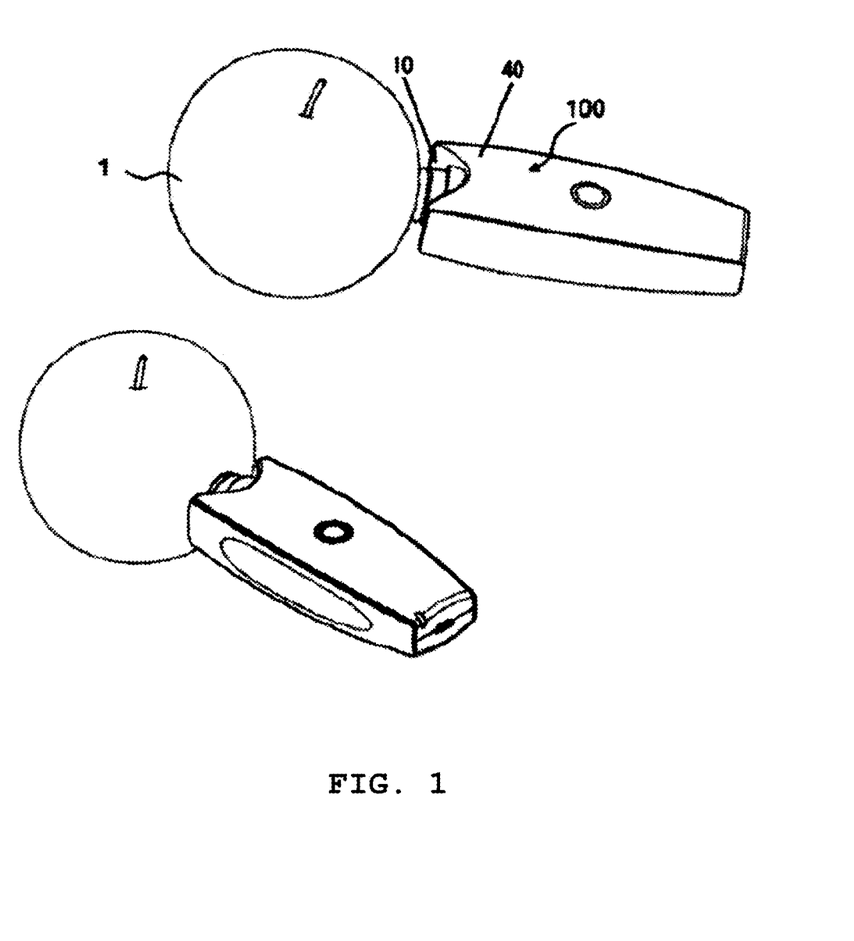
FIG. 1 is a perspective view of a spectroscopic analyzing apparatus according to some embodiments of the present invention, instantiating a measurement of sugar contents of a fruit.
Figure 2:
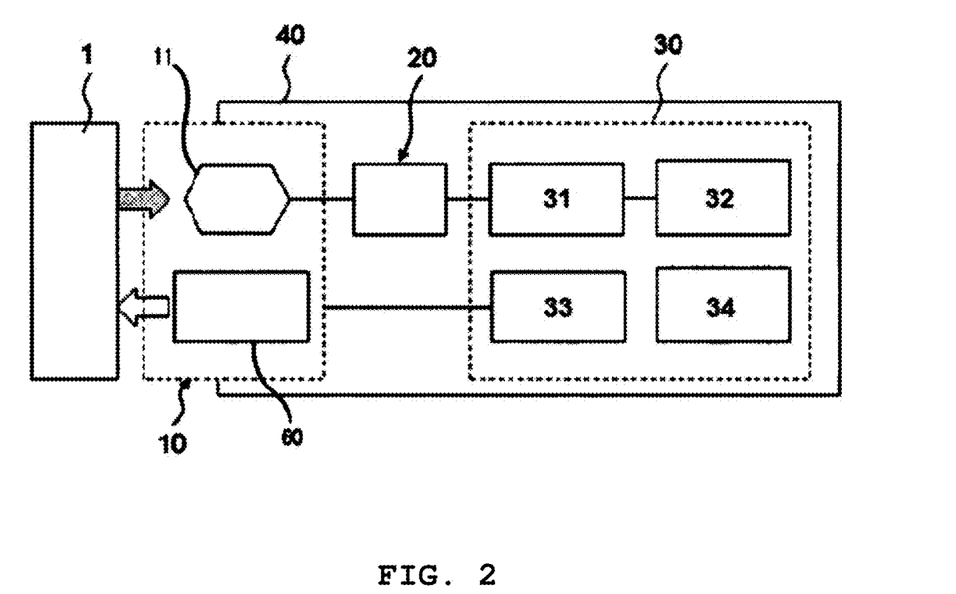
FIG. 2 is a block diagram of the spectroscopic analyzing apparatus.
Figure 3:
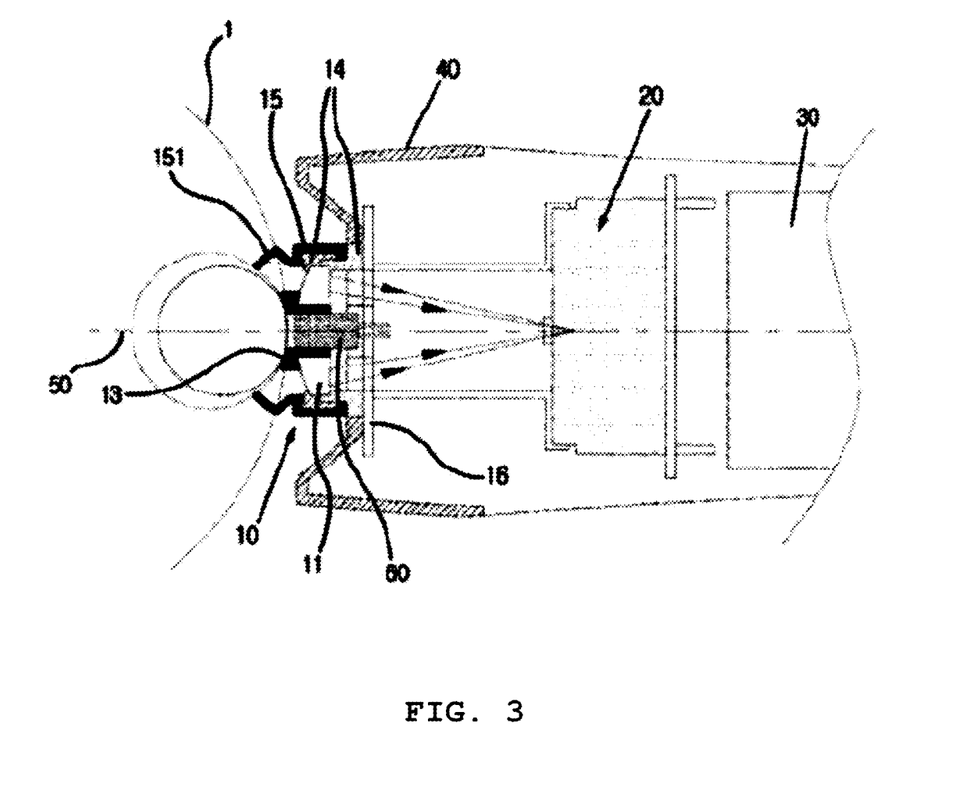
FIG. 3 is a partial cross-sectional view of the spectroscopic analyzing apparatus.
Figure 4:
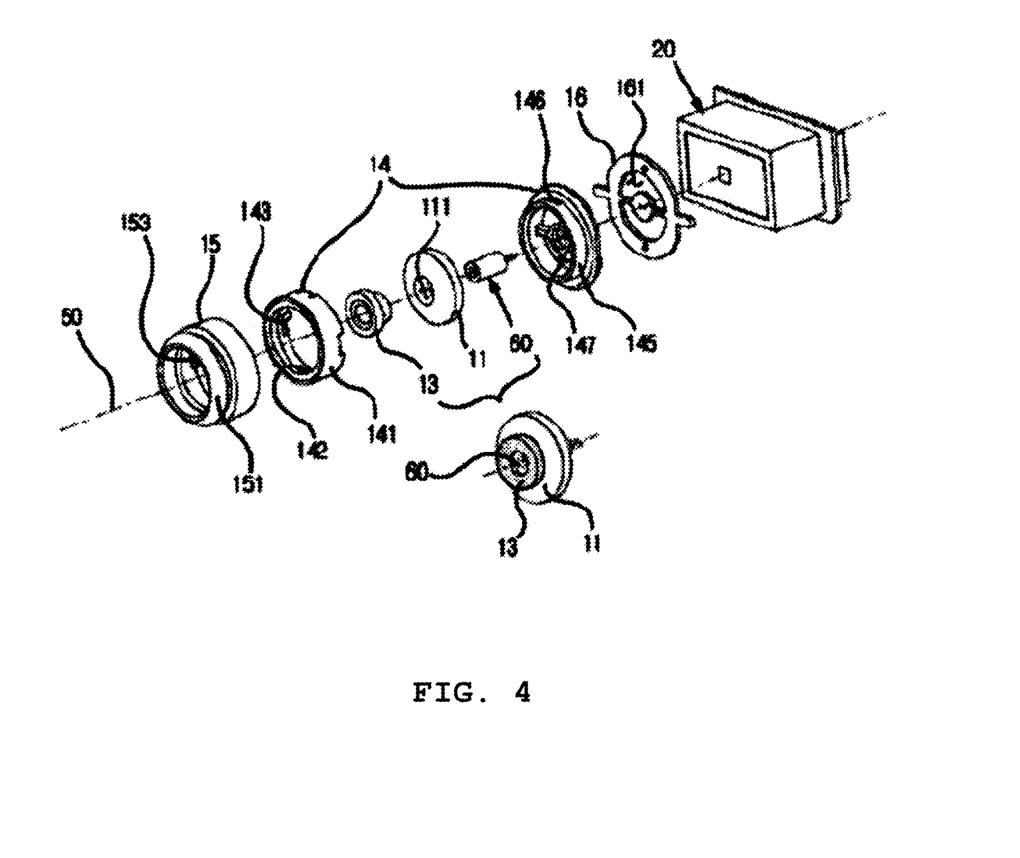
FIG. 4 is an exploded perspective view of the spectroscopic analyzing apparatus.

FIG. 1 is a perspective view of a spectroscopic analyzing apparatus 100 according to some embodiments of the present invention. FIG. 1 instantiates a measurement of sugar contents of a fruit in a nondestructive manner. FIG. 2 is a block diagram of the spectroscopic analyzing apparatus 100. FIG. 3 is a partial cross-sectional view of the spectroscopic analyzing apparatus 100. FIG. 4 is an exploded perspective view of the spectroscopic analyzing apparatus 100.

As shown in FIGS. 1 and 2, the spectroscopic analyzing apparatus 100 includes a body case 40, a head unit 10 arranged at the front end of the body case 40, a spectrometer 20 arranged in the body case 40 at a predetermined distance from the head unit 10, and a controller 30.

The head unit 10 makes contact with a surface of an object 1. In the example shown in FIG. 1, the object 1 is a fruit such as an apple, an orange, or the like, and the spectroscopic analyzing apparatus 100 measures the sugar contents of the fruit in a nondestructive manner.

The head unit 10 includes a lens 11, an external light shielding unit 15, a head case 14, an internal light shielding unit 13, a circuit board 16, and a light source 60.

The light source 60 as a light emitting unit emits near-infrared light to the surface of the object 1. The light emitted from the light source 60 penetrates the object 1 and diffused and reflected from inside the object 1. The lens 11 as a light receiving unit light focuses the diffused and reflected light and transmits the focused light to the spectrometer 20.

The controller 30 includes a light detecting unit 31, a communication unit 32, a light-source driving unit 33, and a power supply unit 34.

The light detecting unit 31 converts an analog signal outputted from the spectrometer 20 to a digital signal to obtain spectrum data.

The communication unit 32 transmits the spectrum data obtained by the light detecting unit 31 to a computer, a smartphone, or the like via a USB connection or a Bluetooth connection.

The power supply unit 34 supplies a power to the electric components of the spectroscopic analyzing apparatus 100, which require an electric power. The controller 30 can additionally perform functions of power driving, switching, and turning on and off various lamps to indicate an operation status.

When measuring the sugar contents of a fruit, for example, a user can hold the fruit with one hand and the body case 40 of the spectroscopic analyzing apparatus 100 with the other hand, keeps the head unit 10 in a manner that the external light shielding unit 15 makes contact with the surface of the fruit, and press a switch (not shown) on the body case 40, to perform a measurement of the sugar contents of the fruit. A beep sound or an indicator can be used to prompt the user to maintain the contact between the external light shielding unit 15 and the fruit.

In some embodiments of the present invention, a space for mounting the light source 60 and a space for mounting the lens 11 are shared to minimize spaces occupied by the light source 60 and the lens 11.

To this end, as shown in FIGS. 3 and 4, the lens 11 includes a through hole 111 at its center, and the light source 60 is arranged in the through hole 111. With this arrangement, the light source 60 and the lens 11 are arranged on the same optical axis.

The internal light shielding unit 13 is formed of an elastic material, such as rubber. The inner surface of the internal light shielding unit 13 makes tight contact with the light source 60, and an outer surface of the internal light shielding unit 13 makes tight contact with the inner wall of the through hole 111, such that even when an impact is applied from the outside, the light source 60 is stably held at the center of the through hole 111.

The internal light shielding unit 13 separates the light source 60 from the lens 11 by a predetermined distance to prevent light reflected at the surface of the object 1 or light diffused and reflected from a shallow depth being incident on the lens 11.

As shown in FIG. 3, an end portion of the internal light shielding unit 13 protrudes from a surface of the lens 11. As the internal light shielding unit 13 is formed of the elastic material, such as rubber, the internal light shielding unit 13 makes contact with the object 1 even when size or curvature of the object 1 varies and securely separates a light emitting area from a light receiving area.

The external light shielding unit 15 is arranged ahead of the body case 40 to cover a portion of the object 1 to be measured. The light source 60 and the lens 11 are arranged on the inner side of the external light shielding unit 15, so that the light source 60 and the lens 11 are shielded from the outside. That is, the external light shielding unit 15 prevents external natural light or scattered light from entering, such that the lens 11 is free from a penetration of such external light.

The external light shielding unit 15 is formed of an elastic material, such as rubber, such that it can be used for various sizes and curvatures of the object 1. In some embodiments of the present invention, the external light shielding unit 15 includes a folding portion 151 that can be folded when an external force is applied.

The light source 60 is connected to the circuit board 16, such that the power supplied by the light-source driving unit 33 of the controller 30 is applied thereto.

The circuit board 16 includes a through hole 161 to allow the light passing through the lens 11 to be incident on the spectrometer 20.

The head case 14 includes a front case 141 and a rear case 145 that can be assembled together. A lens assembly including the light source 60, the lens 11, and the internal light shielding unit 13 is arranged inside the head case 14. The external light shielding unit 15 is coupled to the front of the front case 141, and the circuit board 16 is arranged at the back of the rear case 145.

The front case 141 and the rear case 145 include a hook 142 and a groove 146 that can be coupled to each other, the front case 141 includes a groove 143 to which a protrusion 153 protruded backwardly on the inner side of the external light shielding unit 15 is coupled, and the rear case 145 includes a through hole (not shown) to allow the light passing through the lens 11 to be incident on the spectrometer 20.

Figure 5:
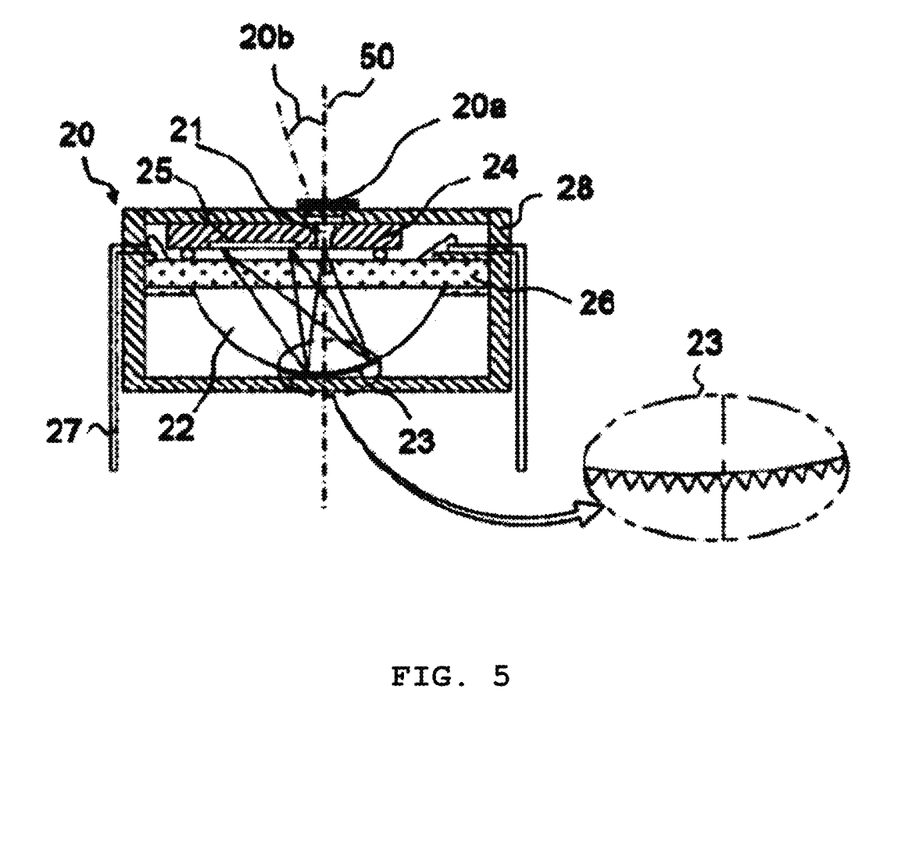
FIG. 5 is a cross-sectional view of a spectrometer according to some embodiments of the present invention.
Figure 6:
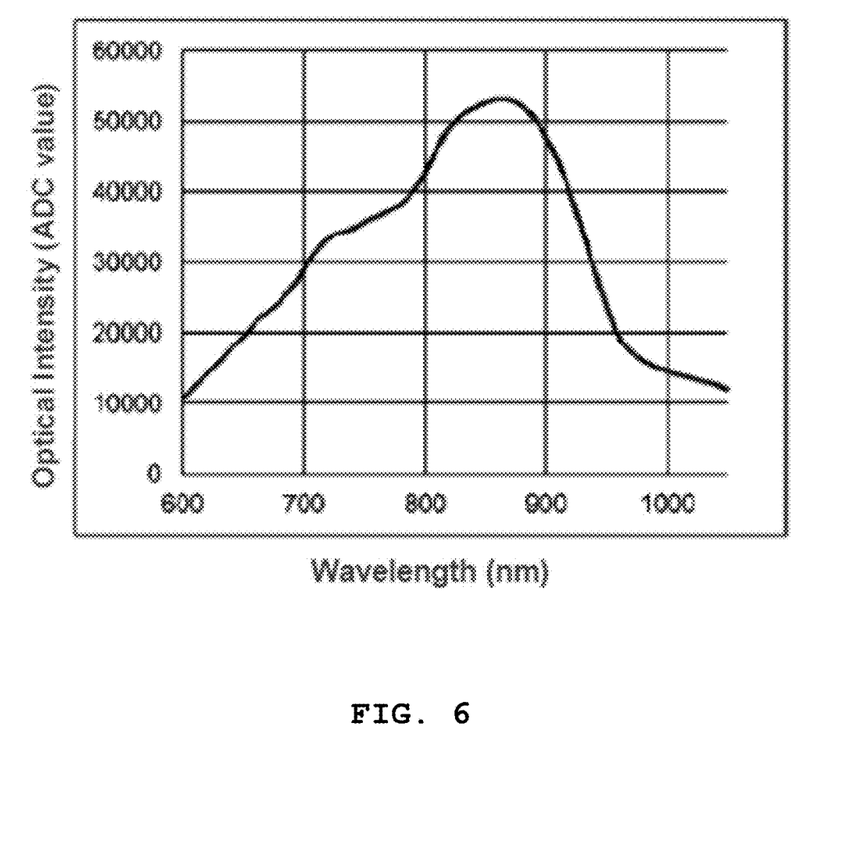
FIG. 6 is a graph showing wavelength spectra as an example of an output signal from the spectrometer shown in FIG. 5.

FIG. 5 is a cross-sectional view of the spectrometer 20. FIG. 6 is a graph showing wavelength spectra as an example of an output signal of the spectrometer 20.

The spectrometer 20 includes a body 28, an input slit 21 arranged to make a straight line with an optical axis 50 on the inner side of the body 28, a silicon substrate 24 in which the input slit 21 is formed, an image sensor 25 mounted on the silicon substrate 24, a transparent glass circuit board 26 coupled to the bottom surface of the silicon substrate 24 and including an electric circuit pattern thereon, a convex lens 22 arranged at the bottom of the transparent glass circuit board 26 and including a diffraction grating 23 on its outer surface, and a lead frame 27 electrically connected to the transparent glass circuit board 26.

The spectrometer 20 further includes a thinfilm optical filter 20a on its optical path. The thinfilm optical filter 20a increases transmissivity of light in a wavelength band having high correlation with a measurement factor of the object 1. This improves the signal-to-noise ratio, thus increasing precision and accuracy of the measurement. In addition, the thinfilm optical filter 20a blocks light in an unnecessary wavelength band, and hence scattered light is suppressed in the spectrometer 20.

The spectrometer 20 is fixed to the body case 40 in a manner that the input slit 21 of the spectrometer 20 is positioned at the focal length of the lens 11 arranged in the head unit 10. In this case, the diameter and the focal length of the lens 11 are determined by the effective incident angle (numerical aperture) 20b of the input slit 21. With this arrangement, the spectrometer 20, the lens 11, and the light source 60 are arranged in a straight line on the optical axis 50.

With the above structure, the light diffused and reflected from inside the object 1 is focused via the lens 11, a light beam passed through the thinfilm optical filter 20a and within the effective incident angle 20b only passes through the input slit 21, and the light diffused with a limited size is separated for each wavelength by the diffraction grating 23 formed on the surface of the convex lens 22, and the light of each wavelength is converted to a photocurrent at each pixel of the image sensor 25, and the spectroscopic spectrum data shown in FIG. 6 are generated at the light detecting unit 31 via the lead frame 27.

Figure 7:
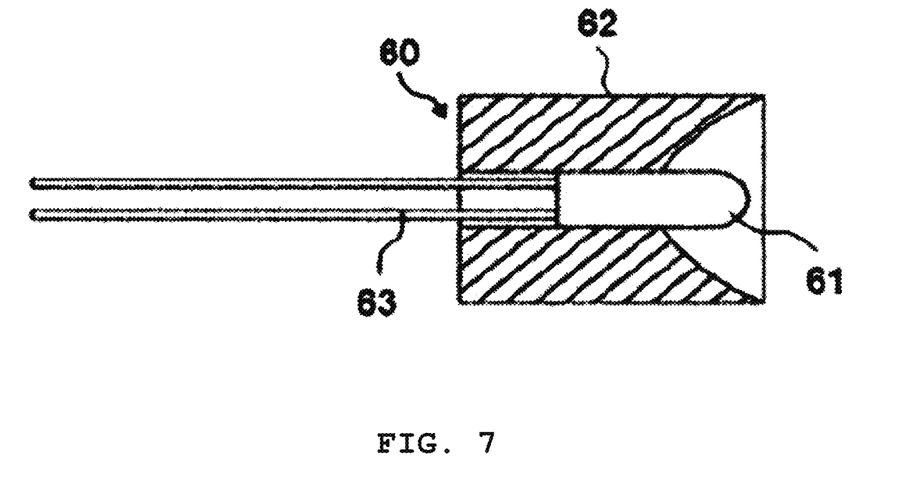
FIG. 7 is a cross-sectional view of a light source according to some embodiments of the present invention.

FIG. 7 is a cross-sectional view of the light source 60.

The light source 60 includes a cylindrical lamp body 62 formed of an aluminum material and a mini lamp 61 fixed with cement or epoxy at the center of the cylindrical lamp body 62. The filament of the mini lamp 61 is designed to be positioned at the focal point (vertex) of an ellipsoidal reflecting plane of the cylindrical lamp body 62 such that light emitted from the filament of the mini lamp 61 is focused toward the object 1.

The spectroscopic analyzing apparatus 100 can downsize the light source 60 and the lens 11 in the head unit 10, and hence the entire shape of the spectroscopic analyzing apparatus 100 has a size compact enough to easily operate by simply making contact with the surface of the object 1.

Figure 8A:
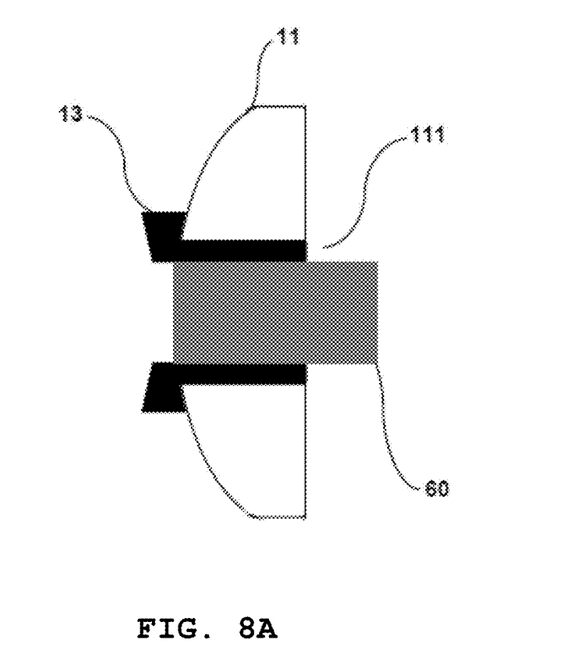
FIG. 8A is a side view of a lens assembly with an integrated light source according to some embodiments of the present invention.
Figure 8B:
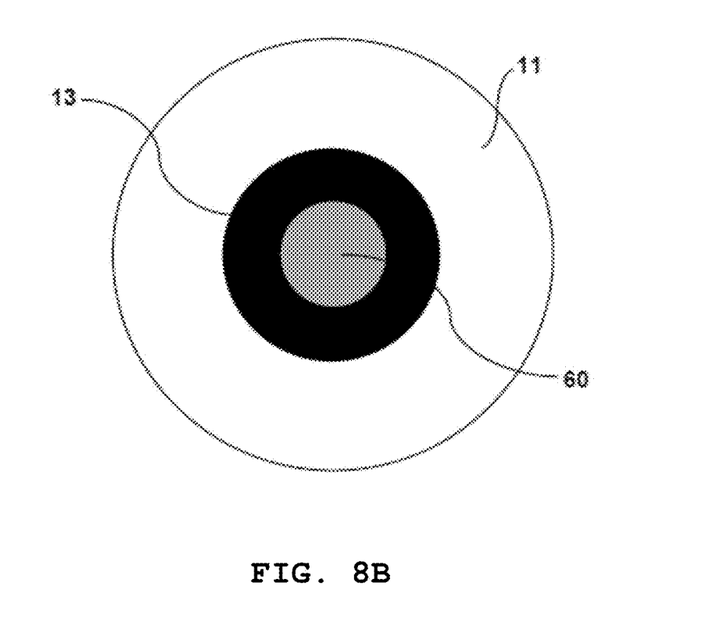
FIG. 8B is a front view of the lens assembly.

FIG. 8A is a side view of the lens assembly with an integrated light source according to some embodiments of the present invention. FIG. 8B is a front view of the lens assembly.

As shown in FIGS. 8A and 8B, the lens assembly with an integrated light source according to some embodiments of the present invention includes light source 60 for emitting the light to the object 1, the lens 11 for receiving and focusing light diffused and reflected from inside the object 1, the through hole 111 formed at the center of the lens 11, in which the light source 60 is arranged, and the internal light shielding unit 13 arranged between the light source 60 and the inner wall of the through hole 111. The front portion of the internal light shielding unit 13 protrudes from the surface of the lens 11 toward the object 1.

According to some embodiments of the present invention, the internal light shielding unit 13 is formed of an elastic material having a property of shielding light and configured to prevent light emitted from the light source 60 and reflected at the surface or a shallow depth of the object 1 from being incident on the lens 11. With this structure, the lens assembly with an integrated light source according to some embodiments of the present invention allows the light diffused and reflected from relatively deep inside the object 1 to be received by the lens 11, while excluding the light reflected at the surface of the shallow depth of the object 1, to improve the efficiency in measuring the internal property of the object 1.

According to some embodiments of the present invention, the internal light shielding unit 13 serves as a fixing member that fixes the light source 60 at the center of the through hole 111. With this structure, the light source 60 can be held at the center of the through hole 111 without any external agent or member to fix the light source 60 at the center of the through hole 111.

According to some embodiments of the present invention, the lens assembly further includes an external light shielding unit 15 (see FIG. 3) surrounding an outer circumference of the lens 11. The front portion of the external light shielding unit 15 protrudes from the surface of the lens 11 toward the object 1.

According to some embodiments of the present invention, the external light shielding unit 15 is formed of an elastic material having a property of shielding light and configured to prevent external natural light or scattered light from being incident on the lens 11. With this structure, the lens assembly with an integrated light source according to some embodiments of the present invention allows the light diffused and reflected from relatively deep inside the object 1 to be received by the lens 11, while preventing any stray light from being incident on the lens 11, to improve the efficiency in measuring the internal property of the object 1.

According to some embodiments of the present invention, the front portion of the external light shielding unit 15 protrudes farther than the front portion of the internal light shielding unit 13 toward the object 1. The external light shielding unit 15 includes a folding portion 151 that is foldable when an external force is applied.

The spectroscopic analyzing apparatus according to some embodiments of the present invention includes a head unit in which a light emitting unit and a light receiving unit are integrated and a compact-sized spectrometer, which can achieve downsizing, light weight, energy saving, and low cost of the apparatus.

In addition, the structure according to some embodiments of the present invention can provide a spectroscopic analyzing apparatus that is portable and carriable, which is a compact and pocket-sized spectroscopic analyzing apparatus that is capable of measuring the internal quality of fruits, drink, food, and the like in a nondestructive manner, for which the internal quality, components, and the like cannot be determined from what one can see.

It is an object of the present invention to provide a spectroscopic analyzing apparatus having a compact structure and high reliability in measurement, which is portable, carriable, and capable of minimizing influence of size and shape of the object and improving the efficiency while increasing the penetration depth of the light.

The spectroscopic analyzing apparatus according to some embodiments of the present invention configured in the above manner has a structure in which the light source as a light emitting unit and the lens as a light receiving unit are arranged at the same position on a plane perpendicular to the optical axis, and hence the spectroscopic analyzing apparatus can be downsized by minimizing the space occupied by the light source and the lens. In addition, the lens and the spectrometer are arranged on the optical axis of the light source, it is less affected by differences in size and shape of the object, and as a result, the penetration of the light can be increase in depth and width. Further, as the internal light shielding unit minimizes the light interference between the light source and the lens, the precision and the accuracy of the spectroscopic measurement can be enhanced with a compact structure.

The present disclosure should not be limited to these embodiments but various changes and modifications are made by one ordinarily skilled in the art within the subject matter, the spirit and scope of the present disclosure as hereinafter claimed. Specific terms used in this disclosure and drawings are used for illustrative purposes and not to be considered as limitations of the present disclosure. Exemplary embodiments of the present disclosure have been described for the sake of brevity and clarity. Accordingly, one of ordinary skill would understand the scope of the claimed invention is not to be limited by the explicitly described above embodiments but by the claims and equivalents thereof.

What is claimed is:

1. A lens assembly with an integrated light source, the lens assembly comprising:
    a light source configured to emit light to an object to be measured;
    a lens configured to receive light diffused and reflected from inside the object;
    a through hole formed at a center of the lens, in which the light source is arranged;
    an internal light shielding unit arranged between the light source and an inner wall of the through hole, wherein a front portion of the internal light shielding unit protrudes from a surface of the lens toward the object; and
    an external light shielding unit surrounding an outer circumference of the lens, wherein
    a front portion of the external light shielding unit protrudes from the surface of the lens toward the object,
    the front portion of the external light shielding unit protrudes farther than the front portion of the internal light shielding unit toward the object, and
    the external light shielding unit includes a folding portion that is foldable when an external force is applied.

2. The lens assembly according to claim 1, wherein the internal light shielding unit is formed of an elastic material having a property of shielding light and configured to prevent light emitted from the light source and reflected at the surface or a shallow depth of the object from being incident on the lens.

3. The lens assembly according to claim 2, wherein the internal light shielding unit serves as a fixing member that fixes the light source at a center of the through hole.

4. The lens assembly according to claim 1, wherein the light source includes a cylindrical lamp body having an ellipsoidal reflecting plane and a light emitting element arranged at a focal point of the ellipsoidal reflecting plane.

5. The lens assembly according to claim 1, wherein the external light shielding unit is formed of an elastic material having a property of shielding light and configured to prevent external natural light or scattered light from being incident on the lens.

6. A spectroscopic analyzing apparatus, comprising:
    a body case;
    a head unit arranged at a first end of the body case;
    a spectrometer arranged in the body case, the spectrometer including an input slit having a predetermined numerical aperture, wherein
    the head unit includes a lens assembly with an integrated light source, and
    the lens assembly includes
        a light source configured to emit light to an object to be measured,
        a lens configured to receive light diffused and reflected from inside the object,
        a through hole formed at a center of the lens, in which the light source is arranged,
        an internal light shielding unit arranged between the light source and an inner wall of the through hole, wherein a front portion of the internal light shielding unit protrudes from a surface of the lens toward the object, and
        an external light shielding unit surrounding an outer circumference of the lens,
    a front portion of the external light shielding unit protrudes from the surface of the lens toward the object,
    the front portion of the external light shielding unit protrudes farther than the front portion of the internal light shielding unit toward the object, and
    the external light shielding unit includes a folding portion that is foldable when an external force is applied.

7. The spectroscopic analyzing apparatus according to claim 6, further comprising:
    a light-source driving unit for driving the light source;
    a light detecting unit for detecting light output from the spectrometer; and
    a communication unit for transmitting an output of the light detecting unit to outside.

8. The spectroscopic analyzing apparatus according to claim 6, further comprising a thinfilm optical filter arranged in front of the input slit of the spectrometer.

9. The spectroscopic analyzing apparatus according to claim 6, wherein the internal light shielding unit is formed of an elastic material having a property of shielding light and configured to prevent light emitted from the light source and reflected at the surface or a shallow depth of the object from being incident on the lens.

10. The spectroscopic analyzing apparatus according to claim 9, wherein the internal light shielding unit serves as a fixing member that fixes the light source at a center of the through hole.

11. The spectroscopic analyzing apparatus according to claim 6, wherein the light source includes a cylindrical lamp body having an ellipsoidal reflecting plane and a light emitting element arranged at a focal point of the ellipsoidal reflecting plane.

12. The spectroscopic analyzing apparatus according to claim 6, wherein the external light shielding unit is formed of an elastic material having a property of shielding light and configured to prevent external natural light or scattered light from being incident on the lens.

* * * * *